United States Patent
Markovits et al.

(10) Patent No.: US 9,321,733 B2
(45) Date of Patent: Apr. 26, 2016

(54) CRYSTALLINE PHARMACEUTICALLY ACTIVE INGREDIENTS

(75) Inventors: Imre Markovits, Budapest (HU); Ferenc Jurak, Budapest (HU); Gyorgyi Kovanyine Lax, Budapest (HU); Csaba Hamori, Budapest (HU); Balazs Havasi, Budapest (HU); Eva Sipos, Budapest (HU); Balazs Volk, Budapest (HU); Zsolt Runge, Budapest (HU); Krisztina Fodorne Kocsmar, Budapest (HU); Gyula Lukacs, Budapest (HU); Katalin Kataine Fadgyas, Budaors (HU); Monika Mezovari, Szigetszentmiklos (HU)

(73) Assignee: EGIS Gyogyszergyar Nyilvanosan Mukodo Reszvenytarsasag, Budapest (HU)

( * ) Notice: Subject to any disclaimer, the term of this patent is extended or adjusted under 35 U.S.C. 154(b) by 113 days.

(21) Appl. No.: 13/885,509

(22) PCT Filed: Nov. 16, 2011

(86) PCT No.: PCT/HU2011/000107
§ 371 (c)(1),
(2), (4) Date: Jul. 15, 2013

(87) PCT Pub. No.: WO2012/066365
PCT Pub. Date: May 24, 2012

(65) Prior Publication Data
US 2013/0296353 A1    Nov. 7, 2013

(30) Foreign Application Priority Data

Nov. 16, 2010   (HU) .................................... 1000616

(51) Int. Cl.
*A61K 31/505*    (2006.01)
*C07D 239/02*    (2006.01)
*C07D 239/42*    (2006.01)

(52) U.S. Cl.
CPC .................................. *C07D 239/42* (2013.01)

(58) Field of Classification Search
CPC ... C07D 239/42; C07D 239/02; A61K 31/505
USPC ......................................... 514/275; 544/297
See application file for complete search history.

(56) References Cited

U.S. PATENT DOCUMENTS

2012/0116082 A1    5/2012   Kovanyin Lax et al.

FOREIGN PATENT DOCUMENTS

| WO | 2008015563 A2 | 2/2008 |
|----|---------------|--------|
| WO | 2009047577 A1 | 4/2009 |
| WO | 2010082072 A1 | 7/2010 |

OTHER PUBLICATIONS

International Search Report from PCT/HU2011/000107 dated Jun. 19, 2012.
M. R. Caira et al. "Crystalline Polymorphism of Organic Compounds" Topics in Current Chemistry, vol. 198, Jan. 1, 1998, pp. 163-208.

*Primary Examiner* — James O Wilson
*Assistant Examiner* — Ebenezer O Sackey
(74) *Attorney, Agent, or Firm* — Millen White Zelano and Branigan, PC; Csaba Henter; Anthony Zelano

(57) ABSTRACT

The present invention is related to crystalline forms of rosuvastatin zinc (2:1) salt. The polymorphs are suitable for use as pharmaceutically active ingredients in the treatment of the diseases of the lipid metabolism including hypercholesterolemia, hyperlipidemia, dyslipidemia or atherosclerosis.

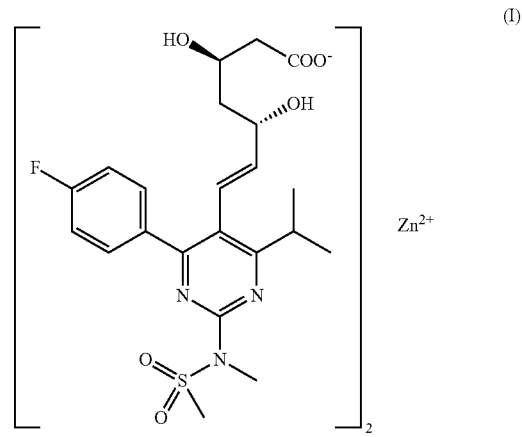

23 Claims, 2 Drawing Sheets

FIG. 1 Powder X-ray diffractogram of crystalline Form V rosuvastatin zinc (2:1) salt
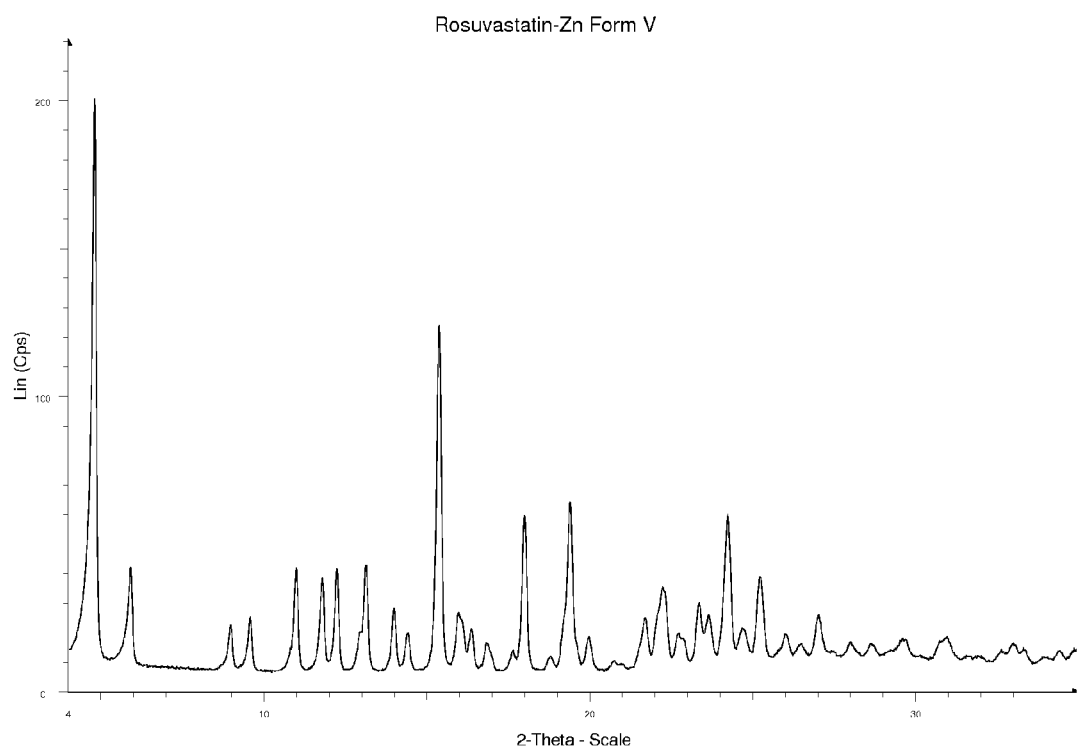

FIG. 2 Powder X-ray diffractogram of crystalline Form III rosuvastatin zinc (2:1) salt
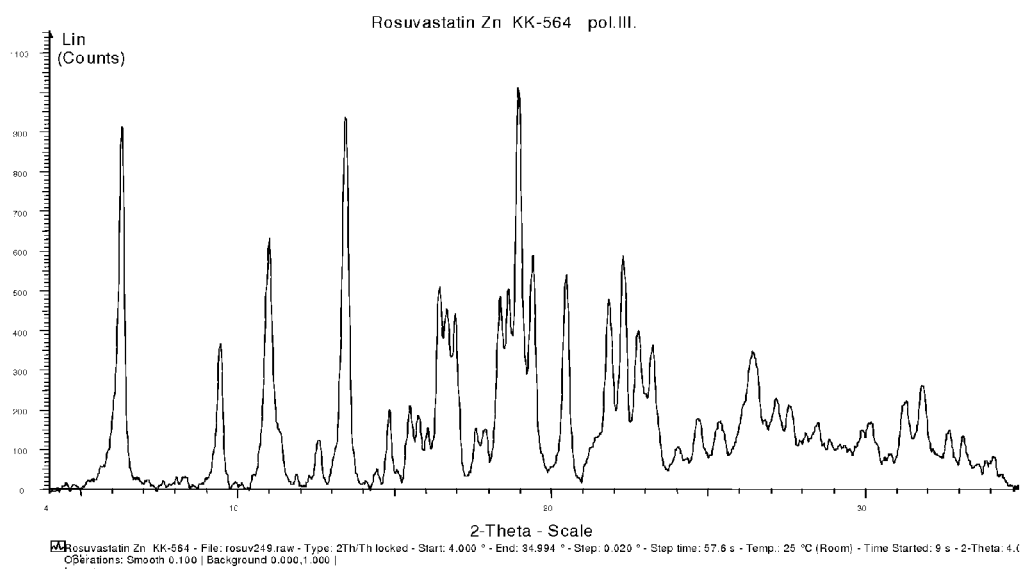

CRYSTALLINE PHARMACEUTICALLY ACTIVE INGREDIENTS

The present invention relates to crystalline forms of the zinc salt of (+)-7-[4-(4-fluorophenyl)-6-isopropyl-2-(methanesulfonyl-methyl-amino)-pyrimidin-5-yl]-(3R,5S)-dihydroxy-hept-6-enoic acid of the Formula (I).

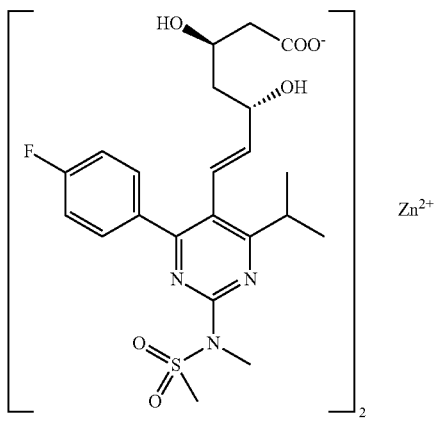

The compound (+)-7-[4-(4-fluorophenyl)-6-isopropyl-2-(methanesulfonyl-methyl-amino)-pyrimidin-5-yl]-(3R,5S)-dihydroxy-hept-6-enoic acid of the Formula (II)

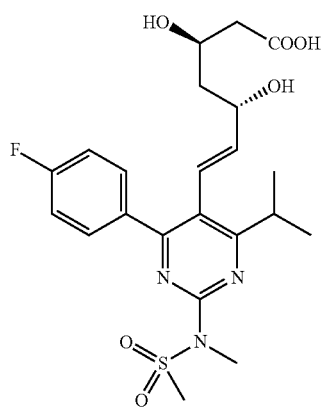

is known by the International Nonproprietary Name rosuvastatin and used in the medicine as a pharmaceutically active ingredient in the treatment of the disorders of the lipid metabolism. Rosuvastatin exerts its activity by inhibiting 2-hydroxy-2-methyl-glutaryl-coenzyme A reductase present in the liver, thus decreasing the rate of the cholesterol biosynthesis in the liver and the cholesterol concentration of the blood. Rosuvastatin, mostly in the form of salts thereof, can be used for the treatment of hypercholesterolemia, hyperlipoproteinemia and atherosclerosis.

The subject of the present invention is crystalline Form V of (+)-7-[4-(4-fluorophenyl)-6-isopropyl-2-(methanesulfonyl-methyl-amino)-pyrimidin-5-yl]-(3R,5S)-dihydroxy-hept-6-enoic acid zinc (2:1) salt of the Formula (I), method for preparation thereof and use thereof in the manufacture of medicaments. Further subject of the present invention is crystalline Form III (+)-7-[4-(4-fluorophenyl)-6-isopropyl-2-(methanesulfonyl-methyl-amino)-pyrimidin-5-yl]-(3R,5S)-dihydroxy-hept-6-enoic acid zinc (2:1) salt of the Formula (I), which can be advantageously used as a starting material during the preparation of crystalline Form V rosuvastatin. A still further object of the present invention is a method for preparing rosuvastatin zinc (2:1) salt in amorphous form.

BACKGROUND OF THE INVENTION (+)-7-[4-(4-fluorophenyl)-6-isopropyl-2-(methanesulfonyl-methyl-amino)-pyrimidin-5-yl]-(3R,5S)-dihydroxy-hept-6-enoic acid of the Formula (II) (rosuvastatin) is known from the state of the art. Rosuvastatin has been disclosed for the first time in European Patent No. 521471 as the free acid and some pharmaceutically acceptable salts thereof, such as the calcium salt of the Formula (III)

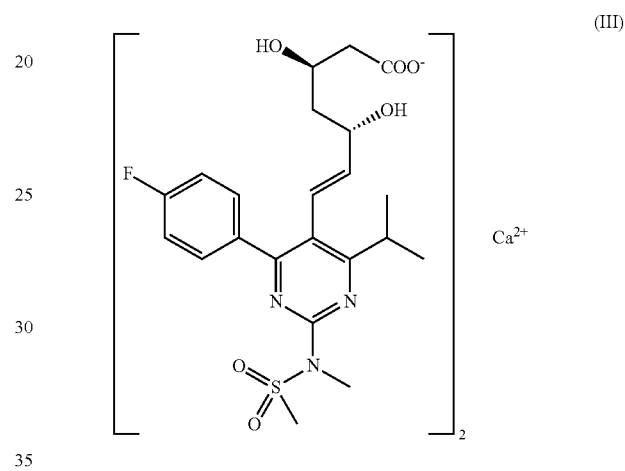

and ammonium salt. Published International Patent Application WO 01/060804 discloses crystalline lithium, magnesium salts of rosuvastatin and crystalline salts of the compound with certain amines. In Published International Patent Applications WO 2005023779, WO 2006079611 and WO 2008036286, several different crystalline hydrate forms of rosuvastatin calcium of the Formula (III) are disclosed. International Patent Applications WO 2005051921 and WO 2008038132 are related to further salts or rosuvastatin with amines or diamines. International Patent Application WO 2005077917 discloses amorphous rosuvastatin magnesium salt. Published International Patent Application WO 2007086082 discloses the amorphous and crystalline potassium salt and the method for the preparation thereof.

Rosuvastatin zinc (2:1) salt of the Formula (I) has been disclosed for the first time in Hungarian Patent Application P0600293 and in the corresponding International Patent Application WO 2007119085. Hungarian Patent Application P070667 and the corresponding Published International Patent Application WO 2009047577 are related to further methods for the preparation of rosuvastatin zinc salt of the Formula (I), wherein rosuvastatin of the Formula (II), sodium salt thereof, an alkyl ester thereof, rosuvastatin lactone or rosuvastatin ketal ester are used as starting materials.

In the International Patent Application WO 2008015563, a method for the preparation of rosuvastatin zinc salt of the Formula (I) has been disclosed, which comprises transforming rosuvastatin tert-butylamine salt into rosuvastatin sodium salt and producing the zinc salt by reacting said rosuvastatin sodium salt with zinc ions and filtering the product from an aqueous solvent.

Hungarian Patent Application P0900019 is related to a further method for the preparation of rosuvastatin zinc salt of the Formula (I), wherein rosuvastatin zinc salt of the Formula (I) is produced directly starting from the tert-butylamine salt of rosuvastatin and isolating said product from an organic solvent.

Rosuvastatin zinc salt of the Formula (I) obtained by the methods of Hungarian Patent Applications P0600293, P070667 and P0900019 or by the method disclosed in International Patent Application WO 2008015563 is of amorphous morphology. International Patent Application PCT/HU2009/00064 is related to crystalline Form I of rosuvastatin zinc (2:1).

The quality of pharmaceutically active ingredients used in medicinal products are determined by strict criteria set forth by health authorities. Some of these criteria is related to the chemical purity and stability of the active ingredient. Further criteria apply to the quality and stability of the medicinal product. These criteria are set forth and published in pharmacopoeias. A basic condition for the issue of the marketing authorization is the compliance with the quality requirements regarding pharmaceutically active ingredients as well as medicinal products.

During the use of rosuvastatin for the manufacture of medicaments, there exists a need for obtaining the pharmaceutically active ingredient in high purity, being chemically stable and in a form which can easily be manipulated during the manufacture of the finished dosage form.

Recently a definite need has arisen in the pharmaceutical industry in order to provide reproducible manufacturing methods for obtaining pharmaceutically active ingredients in chemically and morphologically pure form. Obtaining the pharmaceutically active ingredient in homogeneous solid state is a precondition for complying with the requirements of the industrial manufacture of finished dosage forms. It is a well known fact that solid forms of the same active ingredient having different morphology may exhibit significant differences in the rate of dissolution, bioavailability and chemical stability. From the viewpoint of industrial chemical and pharmaceutical technology, it is important that different solid forms of an active ingredient can possess significantly different properties with regard to the operations of the technology, e.g. rate of filtration or drying, solubility, behaviour during tabletting. The properties mentioned above have a direct impact on the efficiency, economy, reproducibility and complexity of the industrial manufacturing process and at the same time, result in a morphologically homogeneous product.

It is generally accepted that crystalline forms of pharmaceutically active ingredients possess improved chemical stability as compared to the amorphous form. Due to the different decomposition processes during the manufacture and shelf-life of the finished dosage form, this assumption is of general importance. Therefore, manufacturers of medicinal products prefer to use crystalline forms of the active ingredients during pharmaceutical development.

Since active ingredients belonging to the group of statins are explicitly prone to decomposition (Ravi P. Shah, Vijay Kumar and Saranjit Singh, LC-MS/MS Studies on Identification and Characterization of Hydrolytic Products of Atorvastatin, Proceedings of 12th ISMAS Symposium cum Workshop on Mass Spectrometry, Mar. 25-30, 2007, Cidade de Goa, Dona Paula, Goa), there exists a definite need to provide forms of the active ingredients belonging to this group which exhibit increased chemical stability. For example, it is known that the amorphous form of atorvastatin having similar structure to rosuvastatin (i.e. both compounds share the 3,5-dihydroxy-alkanoic acid moiety) or even the morphologically non-homogeneous mixture of amorphous and crystalline forms disclosed in European Patent 409281 are less stable than crystalline forms of the same compound. Thus, development of crystalline forms I, II and IV of atorvastatin showing enhanced properties during chemical or pharmaceutical manipulations (e.g. ease of filtration) and increased stability as disclosed in Published International Patent Application WO 97/03959, initiated development work on behalf of several pharmaceutical companies resulting in the development of more than forty crystalline forms of atorvastatin.

Rosuvastatin is especially prone to decomposition resulting from exposure to light, oxygen and heat. For example, upon light exposure, decomposition products described by Astrarita and coworkers are formed even in solid state (*J. Photochem. Photobiol. A. Chem.* 2007, 187, 263-268).

The polymorphism of a pharmaceutically active ingredient can be exploited in several ways. As discussed above, using a crystalline form having suitable stability and impurity profile (purity) for the manufacture of a finished dosage form is of paramount importance. It is also significant that a crystalline active ingredient should have appropriate properties for manipulations of large-scale manufacturing and pharmaceutical technology on an industrial scale. However, different properties of polymorphs, e.g. dissolution rate, particle size etc. can also be exploited during the design of different finished dosage forms. A polymorph having lower dissolution rate may contribute to the properties of a delayed release dosage form, while the skilled person may appreciate a form having higher solubility or higher dissolution rate during the formulation of an immediate release dosage form.

SUMMARY OF THE INVENTION

According to the above-mentioned facts, there is a strong need to provide crystalline salts of rosuvastatin of the Formula (II).

The objective of our research-development work was to provide rosuvastatin zinc (2:1) salt in a crystalline form, which is amenable to the manufacture of medicaments and can be produced consistently in high quality under industrial circumstances.

The above objective is solved by the present invention.

We have found surprisingly that rosuvastatin zinc (2:1) salt can be synthesized in more than one morphologically homogeneous crystalline forms having suitable stability, advantageous impurity profile and physicochemical properties and which can be manufactured reproducibly on an industrial scale using a simple process.

It is known that crystalline forms of rosuvastatin calcium, disclosed for the first time in 1991, have been available since more than 10 years after the discovery of the amorphous form. Despite the fact that crystalline forms of rosuvastatin calcium have been prepared, said crystalline forms are still not used for the manufacture of medicaments. This phenomenon is reflected in the fact that even the originator product CRESTOR® contains rosuvastatin calcium in amorphous form.

BRIEF DESCRIPTION OF DRAWINGS

FIG. 1: Powder X-ray diffractogram of crystalline Form V rosuvastatin zinc (2:1) salt.

FIG. 2: Powder X-ray diffractogram of crystalline Form III rosuvastatin zinc (2:1) salt.

It is surprising that the zinc (2:1) salt of rosuvastatin can be produced in crystalline form since the formation of complexes of the transitional metal zinc with organic ligands as well as with water or other inorganic compounds and ions, is well known.

Furthermore, there is no method in the state of the art which could be used for predicting the chances of crystal formation for a chemical compound or a salt known only in amorphous form, neither to estimate the physical-chemical properties of a new crystalline form.

According to the first aspect of the present invention, there is provided crystalline Form V of (+)-7-[4-(4-fluorophenyl)-6-isopropyl-2-(methanesulfonyl-methyl-amino)-pyrimidin-5-yl]-(3R,5S)-dihydroxy-hept-6-enoic acid zinc (2:1) salt of the Formula (I).

According to the second aspect of the present invention, there are provided methods for the manufacture of crystalline Form V rosuvastatin zinc (2:1) salt.

According to the third aspect of the invention, there are provided methods for the use of crystalline Form V rosuvastatin zinc (2:1) salt of the Formula (I) for the manufacture of medicaments.

A further aspect of the present invention is the use of crystalline Form V rosuvastatin zinc (2:1) salt for the treatment of the disorders associated with impaired cholesterol and lipid metabolism.

According to a still further aspect of the present invention, there is provided crystalline Form III rosuvastatin zinc (2:1) salt of the Formula (I) which is an advantageous starting material for the manufacture of crystalline Form V rosuvastatin zinc (2:1) salt and a method for preparation thereof.

According to a further aspect of the present invention, there is provided an improved method for the preparation of amorphous rosuvastatin zinc (2:1) salt having high purity.

DETAILED DESCRIPTION OF THE INVENTION

Rosuvastatin zinc (2:1) salt of the Formula (I) produced according to the method disclosed in Hungarian Patent Applications P0600293, P070667 and P0900019 does not have a sharp, well-defined melting point, which indicates an amorphous substance. The melting begins at 137° C. and occurs over a wide temperature range. Rosuvastatin zinc (2:1) salt obtained by the method of International Patent Application WO 2008015563 has been characterized by powder X-ray diffraction analysis. The analytical results disclosed in said patent application clearly indicate that the product obtained has amorphous morphology. No melting point has been disclosed.

We have now surprisingly found that there exist new crystalline forms of rosuvastatin zinc (2:1) salt of the Formula (I).

According to the first aspect of the present invention, there is provided crystalline Form V of (+)-7-[4-(4-fluorophenyl)-6-isopropyl-2-(methanesulfonyl-methyl-amino)-pyrimidin-5-yl]-(3R,5S)-dihydroxy-hept-6-enoic acid zinc salt (2:1) of the Formula (I). Crystalline Form V rosuvastatin zinc (2:1) salt is new.

Crystalline Form V rosuvastatin zinc (2:1) salt exhibits a powder X-ray diffraction pattern (determined using $Cu_K$ radiation) shown in FIG. 1. Characteristic X-ray diffraction angles and the corresponding relative intensities for the crystalline Form V rosuvastatin zinc (2:1) salt are given in Table 1 below.

TABLE 1

X-ray diffraction data of crystalline Form V rosuvastatin zinc (2:1) salt

| 2Theta [°] | d-value [Å] | Relative intensity [%] |
|---|---|---|
| 4.764 | 18.5324 | 100.0 |
| 5.873 | 15.0352 | 20.9 |
| 8.941 | 9.8823 | 11.1 |
| 9.547 | 9.2561 | 12.5 |
| 10.960 | 8.0664 | 20.7 |
| 11.773 | 7.5111 | 19.0 |
| 12.224 | 7.2347 | 20.6 |
| 12.870 | 6.8733 | 8.8 |
| 13.118 | 6.7438 | 21.1 |
| 13.979 | 6.3303 | 13.9 |
| 14.401 | 6.1454 | 9.8 |
| 15.371 | 5.7599 | 61.6 |
| 15.997 | 5.5359 | 13.2 |
| 16.357 | 5.4148 | 10.4 |
| 16.852 | 5.2570 | 8.0 |
| 17.641 | 5.0235 | 6.9 |
| 17.995 | 4.9256 | 29.6 |
| 18.783 | 4.7206 | 5.8 |
| 19.394 | 4.5733 | 31.9 |
| 19.977 | 4.4411 | 9.2 |
| 20.741 | 4.2792 | 5.1 |
| 20.959 | 4.2352 | 4.6 |
| 21.700 | 4.0922 | 12.3 |
| 22.263 | 3.9899 | 17.5 |
| 22.736 | 3.9080 | 9.7 |
| 23.367 | 3.8038 | 14.9 |
| 23.659 | 3.7575 | 12.9 |
| 24.235 | 3.6695 | 29.8 |
| 24.716 | 3.5992 | 10.5 |
| 25.245 | 3.5250 | 19.3 |
| 26.034 | 3.4199 | 9.5 |
| 26.485 | 3.3627 | 8.0 |
| 27.028 | 3.2964 | 12.9 |
| 28.016 | 3.1824 | 8.3 |
| 28.667 | 3.1115 | 8.0 |
| 29.662 | 3.0093 | 8.6 |
| 30.967 | 2.8854 | 9.2 |
| 32.668 | 2.7390 | 6.9 |
| 33.032 | 2.7096 | 8.0 |
| 33.342 | 2.6851 | 7.2 |
| 33.989 | 2.6355 | 5.6 |
| 34.452 | 2.6011 | 6.8 |

Measurement conditions for the powder X-ray diffraction analysis were the following:
Instrument: BRUKER D8 ADVANCE powder X-ray diffractometer
Radiation: $CuK_1$ (1.54060 Å), $CuK_2$ (1.54439 Å)
Voltage: 40 kV
Anode current: 40 mA
Accessories: Göbel-mirror, Soller-slit (2.5°), sampler, transmission position
Detector: LynxEye
Measurement: continuos/scan: 4 −35 2
Acquisition rate: 1.2°/min
Step: 0.02
Sample: without pretreatment, embedded between Mylar sheets, room temperature
Sample rotation: 1 rpm
Reference standard: Quarzprobe RA450 (Bruker AXS)
Reproducibility: ±0.2° 2

It is well known from the state of the art that pretreatment of the sample (e.g. pulverization) can have very significant effect on the relative intensities of the powder X-ray diffractogram. Therefore, no pretreatment of the sample was applied.

The person skilled in the art is in the position to identify the solid-state morphology of a known substance by the powder X-ray diffractograms. This can be carried out simply by determining the position (diffraction angle) of a few intense X-ray diffraction signals. Such an identification is very important for the testing of the morphology of the active ingredient in solid dosage forms, since during the manufacture of the solid finished dosage form, changes of morphology may occur either by transformation of the crystalline active ingredient into a different crystalline modification or into the amorphous form.

The diffraction angle belonging to the most intense diffraction signal of the crystalline Form V rosuvastatin zinc salt (2:1) is 4.764 degrees 2. This X-ray diffraction signal can be the most conveniently used for the identification of crystalline Form I of rosuvastatin zinc (2:1) salt.

Diffraction angles of the diffraction lines where the relative intensity exceeds 50% in the diffractogram of crystalline Form V rosuvastatin zinc (2:1) salt are 4.764 and 15.371 degrees 2.

Diffraction angles belonging to the diffraction signals of crystalline Form V of rosuvastatin zinc (2:1) salt having at least 20% relative intensity are the following: 4.764, 5.873, 10.960, 12.224, 13.118, 15.371, 17.995, 19.394, 24.235 degrees 2.

Crystalline Form V rosuvastatin zinc salt (2:1) of the present invention can contain 1 to 10, preferably 1 to 6 molar equivalents of water either in form of hydrate water, channel hydrate or as physically adsorbed water.

According to the second aspect of the present invention, there is provided a method for the preparation of crystalline Form V rosuvastatin zinc (2:1) salt of the Formula (I).

Throughout the present specification, the meaning of the expression of "an alcohol comprising 1 to 6 carbon atoms" is straight- or branched-chain saturated aliphatic alcohols having 1 to 6 carbon atoms, e.g. methanol, ethanol, 2-propanol, 1-propanol, 1-butanol, 2-butanol and the like.

The method for the preparation of crystalline Form V rosuvastatin zinc (2:1) salt of the Formula (I) comprises stirring rosuvastatin zinc (2:1) salt crystalline Form III in 2 to 100-fold, advantageously 2 to 50-fold, the most preferably 2.5 to 25-fold amount of water or in a mixture of water and an alcohol comprising 1 to 6 carbon atoms at a temperature between −10 and 40° C., preferably between 10-30° C. for 1 to 168 hours, preferably for 4 to 120 hours under inert gas atmosphere. The product is isolated and if desired, dried at a temperature between 0-30° C. under inert atmosphere. Suitable inert gases include but are not limited to nitrogen and argon.

The starting material of the above-mentioned method for the preparation of Form V rosuvastatin zinc (2:1) salt described above is crystalline Form III of rosuvastatin zinc (2:1). Said crystalline form is characterized by the X-ray diffraction data of Table 2 and the X-ray diffractogram of said form is shown in FIG. 2. X-ray diffraction measurements were carried out under identical conditions as described above for crystalline Form V. Crystalline Form III rosuvastatin zinc (2:1) salt can be prepared starting from amorphous rosuvastatin zinc salt.

TABLE 2

Position of the diffraction lines (±0.2°) and relative intensity (>5%) thereof in crystalline Form III rosuvastatin zinc (2:1) salt

| Peak No. | 2 | d (Å) | Intensity (%) |
|---|---|---|---|
| 1 | 6.259 | 14.11083 | 90.2 |
| 2 | 9.400 | 9.40131 | 36 |
| 3 | 10.982 | 8.04997 | 62.4 |

TABLE 2-continued

Position of the diffraction lines (±0.2°) and relative intensity (>5%) thereof in crystalline Form III rosuvastatin zinc (2:1) salt

| Peak No. | 2 | d (Å) | Intensity (%) |
|---|---|---|---|
| 4 | 11.318 | 7.81202 | 15.4 |
| 5 | 12.565 | 7.03939 | 12.1 |
| 6 | 13.414 | 6.59524 | 92.8 |
| 7 | 14.437 | 6.13017 | 5.4 |
| 8 | 14.806 | 5.97820 | 19.6 |
| 9 | 15.48 | 5.71948 | 20.5 |
| 10 | 15.776 | 5.61288 | 18.7 |
| 11 | 16.059 | 5.51479 | 15.4 |
| 12 | 16.401 | 5.40024 | 50.1 |
| 13 | 16.623 | 5.32865 | 44.8 |
| 14 | 16.926 | 5.23406 | 43.6 |
| 15 | 17.572 | 5.04319 | 15.4 |
| 16 | 17.894 | 4.95294 | 15.4 |
| 17 | 18.338 | 4.83405 | 48.9 |
| 18 | 18.600 | 4.76648 | 50.4 |
| 19 | 18.961 | 4.67672 | 100 |
| 20 | 19.409 | 4.56959 | 58.2 |
| 21 | 20.462 | 4.33695 | 53.2 |
| 22 | 21.383 | 4.15201 | 12.6 |
| 23 | 21.846 | 4.06507 | 47.1 |
| 24 | 22.302 | 3.98297 | 58.1 |
| 25 | 22.779 | 3.90066 | 39.5 |
| 26 | 23.232 | 3.82568 | 35.6 |
| 27 | 24.055 | 3.69663 | 10.4 |
| 28 | 24.690 | 3.60288 | 17.4 |
| 29 | 25.388 | 3.50540 | 16.9 |
| 30 | 26.451 | 3.36697 | 33.9 |
| 31 | 27.178 | 3.27846 | 22.5 |
| 32 | 27.603 | 3.22900 | 20.6 |
| 33 | 28.472 | 3.13240 | 16.2 |
| 34 | 29.938 | 2.98221 | 14.8 |
| 35 | 30.180 | 2.95883 | 16.7 |
| 36 | 31.311 | 2.85449 | 21.8 |
| 37 | 31.861 | 2.80646 | 25.7 |
| 38 | 32.695 | 2.73674 | 14.6 |
| 39 | 33.177 | 2.69812 | 13.2 |
| 40 | 34.134 | 2.62459 | 8 |

Crystalline Form III rosuvastatin zinc (2:1) salt can be identified by its principal (basic) reflexion at 18.961 degrees 2 or by the characteristic reflexions exceeding 70% relative intensity at 6.259, 13.414 and 18.961 degrees 2 Characteristic reflexions of crystalline Form III rosuvastatin zinc (2:1) salt exhibiting relative intensity in excess of 50% have been observed at 6.259, 10.982, 13.414, 16.401, 18.600, 18.961, 19.409, 20.462 and 22.302 degrees 2 Crystalline Form III rosuvastatin zinc (2:1) salt exhibits further reflexions having relative intensity larger than 20% at 6.259, 9.400, 10.982, 13.414, 15.480, 16.401, 16.623, 16.926, 18.338, 18.600, 18.961, 19.409, 20.462, 21.846, 22.302, 22.779, 23.232, 26.451, 27.178, 27.603, 31.311 and 31.861 degrees 2

Further objects of the present invention are methods for the preparation of crystalline Form III rosuvastatin zinc (2:1) salt.

The first method for the preparation of crystalline Form III rosuvastatin zinc (2:1) salt comprises stirring amorphous rosuvastatin zinc (2:1) salt at a temperature between −10 and 40° C., preferably between 0 and 10° C. in 5 to 100-fold, preferably 20 to 60-fold weight of water or in a mixture of water and an alcohol comprising 1 to 6 carbon atoms optionally containing 0.0001 to 0.01, preferably 0.005-0.01 molar equivalent amount of sodium hydroxide, calculated for the molar amount of rosuvastatin zinc salt of the Formula (I), for 1 to 48 hours, advantageously 2 to 8 hours, the most preferably for 4 hours, filtering the suspension and optionally washing and drying the product.

The second method for the preparation of crystalline Form III rosuvastatin zinc salt (2:1) resides in stirring amorphous rosuvastatin zinc (2:1) salt in 5 to 100-fold, preferably 20 to 60-fold weight of water or in a mixture of water and an alcohol comprising 1 to 6 carbon atoms at the temperature between −10 and 40° C., preferably between 0 and 10° C. for 1 to 48 hours, advantageously 2 to 8 hours, the most preferably for 4 hours, filtering the product, repeating the stirring in 5 to 100-fold, preferably 20 to 60-fold weight of water or in a mixture of water and an alcohol comprising 1 to 6 carbon atoms at the temperature between −10 and 40° C., preferably between 0 and 10° C. for 1 to 48 hours, advantageously 2 to 8 hours, the most preferably for 4 hours, filtering the suspension and optionally washing and drying the crystalline Form III rosuvastatin zinc (2:1) salt.

According to a still further aspect of the present invention, there is provided a method for the preparation of amorphous rosuvastatin zinc (2:1) salt, which comprises providing a solution of rosuvastatin tert-butylamine salt in water or in a mixture of water and an alcohol comprising 1 to 6 carbon atoms, adding into said solution an aqueous solution of a zinc salt, preferably zinc sulfate at room temperature, and mixing and rapidly mixing and stirring said solution with 2 to 50-fold, preferably 4 to 10-fold volume of water or a mixture of water and an alcohol having 1 to 6 carbon atoms cooled to the temperature between −10 and 20° C., preferably between 0 and 10° C.

According to a further aspect of the present invention, there are provided medicaments containing crystalline Form V rosuvastatin zinc (2:1) salt of the Formula (I). Such medicaments may also contain one or more known vehicles or auxiliary agents.

The medicament according to the present aspect of the invention in most cases contains 0.1 to 95% by weight of the crystalline Form V pharmaceutically active ingredient of the Formula (I). The proportion of the active ingredient is advantageously between 5 to 75% by weight.

Medicaments according to the present invention can be administered orally (e.g. powders, tablets, coated or film-coated tablets, capsules, microcapsules, granules, pellets, dragees, solutions, suspensions or emulsions), parenterally (in the form of e.g. intravenous, intramuscular, subcutaneous or intraperitoneal injections or as an infusion), rectally (e.g. in the form of suppositories) or locally (e.g. as creams, ointments or patches). Solid, semisolid or liquid medicaments according to the present invention can be produced according to methods known from the prior art.

Medicaments suitable for oral administration containing crystalline Form V of rosuvastatin zinc salt (2:1) of the Formula (I) can be presented in solid form, which can contain one or more vehicle or filler (e.g. lactose, glucose, starch, calcium phosphate, microcrystalline cellulose), a binder (e.g. gelatine, sorbitol, polyvinylpyrrolidone), a disintegrant (e.g. croscarmellose, sodium carboxymethylcellulose, crospovidone), tabletting auxiliary agents (e.g. magnesium stearate, talc, polyethylene glycol, silica or silicone dioxide) or surfactants (e.g. sodium lauryl sulfate) besides the active ingredient.

Liquid medicaments intended for oral use containing crystalline Form V of rosuvastatin zinc salt (2:1) according to the present invention can be presented as solutions, suspensions or emulsions and can contain suspending agents (e.g. gelatine, carboxymethylcellulose), emulsifying agents (e.g. sorbitane monooleate), solvents or liquid vehicles (e.g. water, oils, glycerol, propylene glycol, ethanol), pH adjusting agents (e.g. acetate, phosphate, citrate buffers) or stabilizing agents (e.g. methyl-4-hydroxybenzoate) admixed with the active ingredient.

Medicaments containing the crystalline Form V of the compound of the Formula (I) intended for parenteral use are usually sterile isotonic aqueous solutions or suspensions, which can contain a pH adjusting agent and conservants as auxiliary agents.

Medicaments presented as semisolid formulations containing crystalline Form V of the compound of the Formula (I), such as suppositories contain the active ingredient homogeneously dispersed in the semisolid base (e.g. poliethylene glycol, cocoa butter).

Medicaments containing crystalline Form V of rosuvastatin zinc (2:1) salt according to the present invention can be produced as modified release, controlled-release or extended-release formulations. In this manner, long-lasting effect can be achieved or the intervals between the administration of the medicament can be increased. The modified release, controlled release or extended release medicaments can be produced according to the methods known from the prior art.

According to a further aspect of the present invention, there is provided a method for the manufacture of medicaments containing crystalline Form V of rosuvastatin zinc (2:1) salt of the Formula (I), which comprises optionally admixing crystalline Form V of rosuvastatin zinc (2:1) salt with a pharmaceutically acceptable vehicle and an auxiliary agent and transforming the thus obtained product into a pharmaceutical dosage form using the methods known in the art. Suitable pharmaceutically acceptable vehicles and auxiliary agents, as well as formulation methods have been disclosed in the prior art (Remington's Pharmaceutical Sciences, $18^{th}$ Edition, Mack Publishing Co., Easton, USA, 1990).

Medicaments containing crystalline Form V of the compound of the Formula (I) preferably contain the active ingredient in unit dosage forms.

According to a further aspect of the present invention, there is provided a use of crystalline Form V rosuvastatin zinc (2:1) salt of the Formula (I) for the treatment of diseases or disorders associated with the lipid metabolism including hypercholesterolemia, hyperlipoproteinemia, dyslipidemia and atherosclerosis.

According to another aspect of the present invention, there is provided a method for the treatment of diseases or disorders associated with the lipid metabolism, including hypercholesterolemia, hyperlipoproteinemia, dyslipidemia and atherosclerosis, which comprises administering a patient in need of such treatment an effective amount of the crystalline Form V rosuvastatin zinc salt (2:1) of the Formula (I).

Similarly to Form V rosuvastatin zinc (2:1) salt, Form III salt may be used as an active ingredient of pharmaceutical preparations.

Further aspects of the present invention are demonstrated by the following examples without restricting the invention to said examples in any way.

Example 1

Amorphous 7-[4-(4-fluorophenyl)-6-isopropyl-2-(methane-sulfonyl-methylamino)-pyrimidin-5-yl]-(3R,5S)-dihydroxy-hept-6-enoic acid zinc (2:1) salt 50.0 g (0.09 mol) of 7-[4-(4-fluorophenyl)-6-isopropyl-2-(methanesulfonyl-methylamino)-pyrimidin-5-yl]-(3R,5S)-dihydroxy-hept-6-enoic acid tert-butyl-amine salt are dissolved in the mixture of 500 cm³ ethyl acetate and 153 cm³ of distilled water with stirring at 25° C. Into the two-layer mixture thus obtained, 55 cm³ of 2.23 M zinc sulfate solution (corresponding to 0.122 mol $ZnSO_4 \times H_2O$) are added dropwise in 15 minutes at the temperature of 25° C. After 1-hour intense stirring, the layers are separated, the organic layer is washed twice with 100 cm³ of 2.23 M zinc sulfate solution each and finally with 100 cm³ of water. (During the final aqueous washing step, 12 cm³ of ethanol is added to facilitate the separation of the layers.)

Drying of the organic layer is carried out by azeotropic distillation in vacuo at the temperature of 50° C. and at the pressure of 50-70 mbar (approx. 5.0-7.0 kPa) according to the following procedure.

In the first step, almost the total amount of the solvent is distilled off. The residue thus obtained weighed 102.0 g and appears as an oil containing traces of solids. The residue is dissolved in 500 cm³ of ethyl acetate at a temperature of approx. 30° C. and the solvent is distilled off repeatedly until a thick suspension containing solid crystalline phase is obtained. The residue weighing 154 g is dissolved in 300 cm³ of ethyl acetate and the mixture is stirred until homogeneity and the solvent is evaporated until a thick suspension is formed. The suspension weighing 182 g is mixed with 200 cm³ of ethyl acetate and stirred thoroughly. The mixture is filtered, the filtrate is removed thoroughly by suction and suspended on the filter three times with 90 cm³ of ethyl acetate each.

The product is layered carefully in a vacuum drying cabinet protected from light and dried for 24 hours at 25° C. at the pressure of 5 mbar (approx. 0.5 kPa). The product is powdered and dried repeatedly for 6 hours at the temperature of 50° C. and at the pressure of 5 mbar (approx. 0.5 kPa). Thus 41.74 g (90%) product are obtained.

IR (KBr): 3425 (broad), 2969, 1605, 1547, 1510, 1381, 1230, 1197, 1156, 965, 901, 844, 811, 776, 576, 567, 520 cm$^{-1}$ Melting point: starts melting from 137° C.
Water: 0.85%.

Example 2

Amorphous 7-[4-(4-fluorophenyl)-6-isopropyl-2-(methanesulfonyl-methylamino)-pyrimidin-5-yl]-(3R,5S)-dihydroxy-hept-6-enoic acid zinc (2:1) salt 12.4 g of rosuvastatin tert butyl amine salt is suspended in the mixture of 40 cm³ 2-propanol and 5 cm³ water. To this suspension a solution of 4.4 g ZnSO$_4$ and 15 ml water is added, then almost clear solution is formed. This solution is added to 320 cm³ water at 4-6° C. during 5 minutes. After 0.5 hours stirring period at 4-6° C. it is filtered, then the cake is dried at 25° C. in vacuum under inert atmosphere.

Example 3

Amorphous 7-[4-(4-fluorophenyl)-6-isopropyl-2-(methanesulfonyl-methylamino)-pyrimidin-5-yl]-(3R,5S)-dihydroxy-hept-6-enoic acid zinc (2:1) salt 10.0 g of amorphous or crystalline form I rosuvastatin zinc (2:1) salt is dissolved in the mixture of 35 cm³ 2-propanol and 15 cm³ water. This solution is added to 320 cm³ water at 4-6° C. during 5 minutes. After 0.5 hours stirring period at 4-6° C. it is filtered, then the cake is dried at 25° C. in vacuum under inert atmosphere.

Example 4

Amorphous 7-[4-(4-fluorophenyl)-6-isopropyl-2-(methanesulfonyl-methylamino)-pyrimidin-5-yl]-(3R,5S)-dihydroxy-hept-6-enoic acid zinc (2:1) salt 10.0 g of rosuvastatin tert butyl amine salt is dissolved in 600 cm³ water. The solution is cooled to 0-5° C. Then to the cooled solution the solution of 3.6 g ZnSO$_4$ and 15 ml water is added. The suspension is stirred for 0.5 hours at 4-6° C., then it is filtered, the cake is dried at 25° C. in vacuum under inert atmosphere.

Example 5

Amorphous 7-[4-(4-fluorophenyl)-6-isopropyl-2-(methanesulfonyl-methylamino)-pyrimidin-5-yl]-(3R,5S)-dihydroxy-hept-6-enoic acid zinc (2:1) salt 10.0 g of rosuvastatin tert butyl amine salt is dissolved in the mixture of 36 cm³ 2-propanol and 340 cm³ water. The solution is cooled to 0-5° C., then to the cooled solution the solution of 3.6 g ZnSO$_4$ and 15 ml water is added. The suspension is stirred for 0.5 hours at 4-6° C., then it is filtered, the cake is dried at 25° C. in vacuum under inert atmosphere.

Example 6

Crystalline Form III 7-[4-(4-fluorophenyl)-6-isopropyl-2-(methanesulfonyl-methylamino)-pyrimidin-5-yl]-(3R,5S)-dihydroxy-hept-6-enoic acid zinc (2:1) salt 1.0 g (0.97 mmol) of amorphous rosuvastatin zinc (2:1) salt prepared according to Example 1 is added to the solution of 0.2 mg (0.005 mmol) sodium hydroxide in 40 cm³ of distilled water. The mixture is stirred for 4 hours at the temperature of 40° C. in an argon atmosphere, filtered and washed with a solution having the same composition as the suspending agent. The thus obtained wet cake is repeatedly stirred for 4 hours under the same conditions as in the first period. The suspension is filtered, washed with a solution having the same composition as the suspending solution and dried in a vacuum drying cabinet at the temperature of 25 to 27° C. at the pressure of 5 mbar (0.5 kPa) for 24 hours. Thus 0.75 g (75%) product is obtained having the X-ray diffraction pattern demonstrated in FIG. 2.

Melting point: 110-120° C.
Purity (by HPLC): 99.71%.
Zinc content: 6.25% (98.4% of the theoretical).

Example 7

Crystalline Form III 7-[4-(4-fluorophenyl)-6-isopropyl-2-(methanesulfonyl-methylamino)-pyrimidin-5-yl]-(3R,5S)-dihydroxy-hept-6-enoic acid zinc (2:1) salt 10.0 g of amorphous rosuvastatin zinc (2:1) salt prepared according to Example 1 is suspended in 600 cm³ water for 24 hours, at 4-6° C. Then it is filtered, and the cake is dried at 25° C. in vacuum under inert atmosphere.

Example 8

Crystalline Form III 7-[4-(4-fluorophenyl)-6-isopropyl-2-(methanesulfonyl-methylamino)-pyrimidin-5-yl]-(3R,5S)-dihydroxy-hept-6-enoic acid zinc (2:1) salt 10.0 g of amorphous rosuvastatin zinc (2:1) salt prepared according to Example 1 is suspended in the mixture of 36 cm³ 2-propanol and 350 cm³ water for 24 hours, at 4-6° C. Then it is filtered, and the cake is dried at 25° C. in vacuum under inert atmosphere.

Example 9

Crystalline Form V 7-[4-(4-fluorophenyl)-6-isopropyl-2-(methanesulfonyl-methylamino)-pyrimidin-5-yl]-(3R,5S)-dihydroxy-hept-6-enoic acid zinc (2:1) salt 2.0 g of rosuvastatin zinc (2:1) salt Form III polymorph are dissolved in water at 25° C. and the mixture is stirred for 24 hours under argon atmosphere. Thereafter the mixture is cooled to 3° C. and the stirring is continued for additional 96 hours. The solid product is filtered and dried at 25° C. under argon atmosphere.

Example 10

Crystalline Form V 7-[4-(4-fluorophenyl)-6-isopropyl-2-(methanesulfonyl-methylamino)-pyrimidin-5-yl]-(3R,5S)-dihydroxy-hept-6-enoic acid zinc (2:1) salt 2.0 g of rosuvastatin zinc (2:1) salt Form III polymorph are suspended in of 7 cm$^3$ 2-propanol and 70 cm$^3$ water at 25° C. and the mixture is stirred for 24 hours under argon atmosphere. The solid product is filtered and dried at 25° C. in vacuum under inert atmosphere.

Example 11

Crystalline Form V 7-[4-(4-fluorophenyl)-6-isopropyl-2-(methanesulfonyl-methylamino)-pyrimidin-5-yl]-(3R,5S)-dihydroxy-hept-6-enoic acid zinc (2:1) salt 2.0 g of rosuvastatin zinc (2:1) salt Form III polymorph are suspended in 20 cm$^3$ of water at 25° C. and the mixture is stirred for 24 hours under argon atmosphere. Thereafter the mixture is cooled to 3° C. and the stirring is continued for additional 96 hours. The solid product is filtered and dried at 25° C. under in vacuum inert atmosphere.

What we claim is:

1. A crystalline Form V rosuvastatin zinc (2:1) salt [hemizinc salt of (+)-7-[4-(4-fluorophenyl)-6-isopropyl-2-(methanesulfonyl-methyl-amino)-pyrimidin-5-yl]-(3R,5S)-dihydroxy-hept-6-enoic acid] of Formula (I)

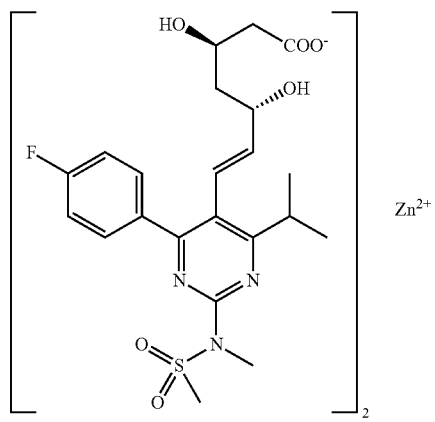

which has
X-ray diffraction lines measured by CuKα radiation at the following diffraction angle 2Θ (±0.2° 2Θ): 4.746 degrees;
or
X-ray diffraction lines measured by CuKα radiation at the following diffraction angles 2Θ (±0.2° 2Θ): 4.746 and 15.371 degrees;
or
a powder X-ray diffractogram of FIG. 1;
or
the following X-ray diffraction lines measured by the CuKα radiation:

| 2Θ [°] | d-value [Å] | Relative intensity [%] |
|---|---|---|
| 4.764 | 18.5324 | 100.0 |
| 5.873 | 15.0352 | 20.9 |
| 8.941 | 9.8823 | 11.1 |
| 9.547 | 9.2561 | 12.5 |
| 10.960 | 8.0664 | 20.7 |
| 11.773 | 7.5111 | 19.0 |
| 12.224 | 7.2347 | 20.6 |
| 12.870 | 6.8733 | 8.8 |
| 13.118 | 6.7438 | 21.1 |
| 13.979 | 6.3303 | 13.9 |
| 14.401 | 6.1454 | 9.8 |
| 15.371 | 5.7599 | 61.6 |
| 15.997 | 5.5359 | 13.2 |
| 16.357 | 5.4148 | 10.4 |
| 16.852 | 5.2570 | 8.0 |
| 17.641 | 5.0235 | 6.9 |
| 17.995 | 4.9256 | 29.6 |
| 18.783 | 4.7206 | 5.8 |
| 19.394 | 4.5733 | 31.9 |
| 19.977 | 4.4411 | 9.2 |
| 20.741 | 4.2792 | 5.1 |
| 20.959 | 4.2352 | 4.6 |
| 21.700 | 4.0922 | 12.3 |
| 22.263 | 3.9899 | 17.5 |
| 22.736 | 3.9080 | 9.7 |
| 23.367 | 3.8038 | 14.9 |
| 23.659 | 3.7575 | 12.9 |
| 24.235 | 3.6695 | 29.8 |
| 24.716 | 3.5992 | 10.5 |
| 25.245 | 3.5250 | 19.3 |
| 26.034 | 3.4199 | 9.5 |
| 26.485 | 3.3627 | 8.0 |
| 27.028 | 3.2964 | 12.9 |
| 28.016 | 3.1824 | 8.3 |
| 28.667 | 3.1115 | 8.0 |
| 29.662 | 3.0093 | 8.6 |
| 30.967 | 2.8854 | 9.2 |
| 32.668 | 2.7390 | 6.9 |
| 33.032 | 2.7096 | 8.0 |
| 33.342 | 2.6851 | 7.2 |
| 33.989 | 2.6355 | 5.6 |
| 34.452 | 2.6011 | 6.8. |

2. A crystalline Form V rosuvastatin zinc (2:1) salt [hemizinc salt of (+)-7-[4-(4-fluorophenyl)-6-isopropyl-2-(methanesulfonyl-methyl-amino)-pyrimidin-5-yl]-(3R,5S)-dihydroxy-hept-6-enoic acid] of the Formula (I) according to claim 1, which has X-ray diffraction lines measured by CuKα radiation at the following diffraction angles 2Θ (±0.2° 2Θ): 4.746 and 15.371 degrees.

3. A crystalline Form V rosuvastatin zinc salt (2:1) according to claim 1 having the following X-ray diffraction lines measured by CuKα radiation:

| 2Θ [°] | d-value [Å] | Relative intensity [%] |
|---|---|---|
| 4.764 | 18.5324 | 100.0 |
| 5.873 | 15.0352 | 20.9 |

-continued

| 2Θ [°] | d-value [Å] | Relative intensity [%] |
|---|---|---|
| 8.941 | 9.8823 | 11.1 |
| 9.547 | 9.2561 | 12.5 |
| 10.960 | 8.0664 | 20.7 |
| 11.773 | 7.5111 | 19.0 |
| 12.224 | 7.2347 | 20.6 |
| 12.870 | 6.8733 | 8.8 |
| 13.118 | 6.7438 | 21.1 |
| 13.979 | 6.3303 | 13.9 |
| 14.401 | 6.1454 | 9.8 |
| 15.371 | 5.7599 | 61.6 |
| 15.997 | 5.5359 | 13.2 |
| 16.357 | 5.4148 | 10.4 |
| 16.852 | 5.2570 | 8.0 |
| 17.641 | 5.0235 | 6.9 |
| 17.995 | 4.9256 | 29.6 |
| 18.783 | 4.7206 | 5.8 |
| 19.394 | 4.5733 | 31.9 |
| 19.977 | 4.4411 | 9.2 |
| 20.741 | 4.2792 | 5.1 |
| 20.959 | 4.2352 | 4.6 |
| 21.700 | 4.0922 | 12.3 |
| 22.263 | 3.9899 | 17.5 |
| 22.736 | 3.9080 | 9.7 |
| 23.367 | 3.8038 | 14.9 |
| 23.659 | 3.7575 | 12.9 |
| 24.235 | 3.6695 | 29.8 |
| 24.716 | 3.5992 | 10.5 |
| 25.245 | 3.5250 | 19.3 |
| 26.034 | 3.4199 | 9.5 |
| 26.485 | 3.3627 | 8.0 |
| 27.028 | 3.2964 | 12.9 |
| 28.016 | 3.1824 | 8.3 |
| 28.667 | 3.1115 | 8.0 |
| 29.662 | 3.0093 | 8.6 |
| 30.967 | 2.8854 | 9.2 |
| 32.668 | 2.7390 | 6.9 |
| 33.032 | 2.7096 | 8.0 |
| 33.342 | 2.6851 | 7.2 |
| 33.989 | 2.6355 | 5.6 |
| 34.452 | 2.6011 | 6.8 |

4. A rosuvastatin zinc (2:1) salt according to claim 1, having a powder X-ray diffractogram of FIG. 1 measured by CuKα radiation.

5. A rosuvastatin zinc (2:1) salt according to claim 1, containing 1 to 10 moles of water.

6. A mixture of crystalline rosuvastatin zinc (2:1) salt according to claim 1 and amorphous rosuvastatin zinc (2:1) salt.

7. A method for preparing crystalline Form V rosuvastatin zinc (2:1) salt according to claim 1, comprising stirring amorphous rosuvastatin zinc (2:1) salt at a temperature between −10 and 40° C. in 5 to 100-fold weight of water or in a mixture of water and an alcohol comprising 1 to 6 carbon atoms optionally containing 0.0001 to 0.01 molar equivalent amount of sodium hydroxide, calculated for the molar amount of rosuvastatin zinc salt of the Formula (I), for 1 to 48 hours, filtering the suspension, optionally repeating the stirring in 5 to 100-fold weight of water or in a mixture of water and an alcohol comprising 1 to 6 carbon atoms at a temperature between −10 and 40° C. for 1 to 48 hours, and optionally washing and drying the resultant product, which is crystalline Form III rosuvastatin zinc (2:1) salt, stirring the thus obtained product in 2 to 100-fold amount of water or in a mixture of water and an alcohol comprising 1 to 6 carbon atoms at a temperature between −10 and 40° C. for 1 to 168 hours, and isolating and optionally drying the product, which is crystalline Form V rosuvastatin zinc (2:1) salt.

8. A method for preparing crystalline Form V rosuvastatin zinc (2:1) salt of the Formula (I) according to claim 1, comprising stirring rosuvastatin zinc (2:1) salt crystalline Form III in 2 to 100-fold amount of water or in a mixture of water and an alcohol comprising 1 to 6 carbon atoms at a temperature between −10 and 40° C. for 1 to 168 hours, and isolating and optionally drying the product.

9. A method according to claim 8, wherein the stirring, isolation and optional drying is carried out under an inert gas atmosphere.

10. A method according to claim 8, wherein the drying is carried out at a temperature between 0 and 30° C.

11. A pharmaceutical composition, comprising crystalline Form V rosuvastatin zinc (2:1) salt according to claim 1, and a pharmaceutically acceptable vehicle.

12. A method for preparing a pharmaceutical composition according to claim 11, comprising mixing crystalline Form V rosuvastatin zinc salt with a pharmaceutically acceptable vehicle and formulating the resultant composition into a pharmaceutical dosage form.

13. A method for therapy, comprising administering to a subject in need thereof an effective amount of a crystalline Form V rosuvastatin zinc salt (2:1) according to claim 1.

14. A method for treating lipid metabolism, hypercholesterolemia, hyperlipidemia, dyslipidemia or atherosclerosis, comprising administering to a subject in need thereof an effective amount of a crystalline Form V rosuvastatin zinc salt (2:1) according to claim 1.

15. A method for treating a disorder in lipid metabolism, hypercholesterolemia, hyperlipidemia, dyslipidemia or atherosclerosis, comprising administering to a subject in need thereof an effective amount of a crystalline Form V rosuvastatin zinc salt (2:1) according to claim 1.

16. A method according to claim 8, wherein the crystalline Form III rosuvastatin zinc (2:1) salt [hemizinc salt of (+)-7-[4-(4-fluorophenyl)-6-isopropyl-2-(methanesulfonyl-methyl-amino)-pyrimidin-5-yl]-(3R,5S)-dihydroxy-hept-6-enoic acid] is of Formula (I)

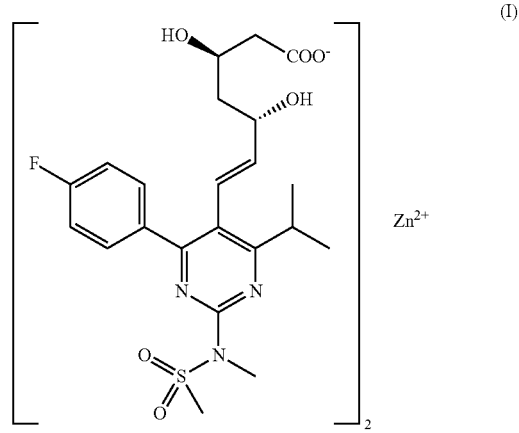

which has

X-ray diffraction line measured by CuKα radiation at the following diffraction angles 2Θ (±0.2° 2Θ): 18.961 degrees;

or

X-ray diffraction lines measured by CuKα radiation at the following diffraction angles 2Θ (±0.2° 2Θ): 6.259, 13.414 and 18.961 degrees;

or

X-ray diffraction lines measured by CuKα radiation at the following diffraction angles 2Θ (±0.2° 2Θ): 6.259, 10.982, 13.414, 16.401, 18.600, 18.961, 19.409, 20.462 and 22.302 degrees;

or

X-ray diffraction lines measured by CuKα radiation at the following diffraction angles 2Θ (±0.2° 2Θ): 6.259, 9.400, 10.982, 13.414, 15.480, 16.401, 16.623, 16.926, 18.338, 18.600, 18.961, 19.409, 20.462, 21.846, 22.302, 22.779, 23.232, 26.451, 27.178, 27.603, 31.311 and 31.861 degrees;

or a powder X-ray diffractogram of FIG. 2 measured by CuKα radiation;

or characteristic reflexions in a powder X-ray diffractogram measured by CuKα radiation according to the following table:

| 2Θ | d (Å) | Relative Intensity (%) |
| --- | --- | --- |
| 6.259 | 14.11083 | 90.2 |
| 9.400 | 9.40131 | 36 |
| 10.982 | 8.04997 | 62.4 |
| 11.318 | 7.81202 | 15.4 |
| 12.565 | 7.03939 | 12.1 |
| 13.414 | 6.59524 | 92.8 |
| 14.437 | 6.13017 | 5.4 |
| 14.806 | 5.97820 | 19.6 |
| 15.48 | 5.71948 | 20.5 |
| 15.776 | 5.61288 | 18.7 |
| 16.059 | 5.51479 | 15.4 |
| 16.401 | 5.40024 | 50.1 |
| 16.623 | 5.32865 | 44.8 |
| 16.926 | 5.23406 | 43.6 |
| 17.572 | 5.04319 | 15.4 |
| 17.894 | 4.95294 | 15.4 |
| 18.338 | 4.83405 | 48.9 |
| 18.600 | 4.76648 | 50.4 |
| 18.961 | 4.67672 | 100 |
| 19.409 | 4.56959 | 58.2 |
| 20.462 | 4.33695 | 53.2 |
| 21.383 | 4.15201 | 12.6 |
| 21.846 | 4.06507 | 47.1 |
| 22.302 | 3.98297 | 58.1 |
| 22.779 | 3.90066 | 39.5 |
| 23.232 | 3.82568 | 35.6 |
| 24.055 | 3.69663 | 10.4 |
| 24.690 | 3.60288 | 17.4 |
| 25.388 | 3.50540 | 16.9 |
| 26.451 | 3.36697 | 33.9 |
| 27.178 | 3.27846 | 22.5 |
| 27.603 | 3.22900 | 20.6 |
| 28.472 | 3.13240 | 16.2 |
| 29.938 | 2.98221 | 14.8 |
| 30.180 | 2.95883 | 16.7 |
| 31.311 | 2.85449 | 21.8 |
| 31.861 | 2.80646 | 25.7 |
| 32.695 | 2.73674 | 14.6 |
| 33.177 | 2.39812 | 13.2 |
| 34.134 | 2.62459 | 8. |

17. A method according to claim 16, wherein the crystalline Form III rosuvastatin zinc (2:1) salt [hemizinc salt of (+)-7-[4-(4-fluorophenyl)-6-isopropyl-2-(methanesulfonyl-methyl-amino)-pyrimidin-5-yl]-(3R,5S)-dihydroxy-hept-6-enoic acid] of the Formula (I) has X-ray diffraction lines measured by CuKα radiation at the following diffraction angles 2Θ (±0.2° 2Θ): 6.259, 13.414 and 18.961 degrees.

18. A method according to claim 16, wherein the crystalline Form III rosuvastatin zinc (2:1) salt [hemizinc salt of (+)-7-[4-(4-fluorophenyl)-6-isopropyl-2-(methanesulfonyl-methyl-amino)-pyrimidin-5-yl]-(3R,5S)-dihydroxy-hept-6-enoic acid] of the Formula (I) has X-ray diffraction lines measured by CuKα radiation at the following diffraction angles 2Θ (±0.2° 2Θ): 6.259, 10.982, 13.414, 16.401, 18.600, 18.961, 19.409, 20.462 and 22.302 degrees.

19. A method according to claim 16, wherein the crystalline Form III rosuvastatin zinc (2:1) salt [hemizinc salt of (+)-7-[4-(4-fluorophenyl)-6-isopropyl-2-(methanesulfonyl-methyl-amino)-pyrimidin-5-yl]-(3R,5S)-dihydroxy-hept-6-enoic acid] of the Formula (I) has X-ray diffraction lines measured by CuKα radiation at the following diffraction angles 2Θ (±0.2° 2Θ): 6.259, 9.400, 10.982, 13.414, 15.480, 16.401, 16.623, 16.926, 18.338, 18.600, 18.961, 19.409, 20.462, 21.846, 22.302, 22.779, 23.232, 26.451, 27.178, 27.603, 31.311 and 31.861 degrees.

20. A method according to claim 16, wherein the crystalline Form III rosuvastatin zinc (2:1) salt has a powder X-ray diffractogram of FIG. 2 measured by CuKα radiation.

21. A method according to claim 16, wherein the crystalline Form III rosuvastatin zinc (2:1) salt has characteristic reflexions in a powder X-ray diffractogram measured by CuKα radiation according to the following table:

| 2Θ | d (Å) | Relative Intensity (%) |
| --- | --- | --- |
| 6.259 | 14.11083 | 90.2 |
| 9.400 | 9.40131 | 36 |
| 10.982 | 8.04997 | 62.4 |
| 11.318 | 7.81202 | 15.4 |
| 12.565 | 7.03939 | 12.1 |
| 13.414 | 6.59524 | 92.8 |
| 14.437 | 6.13017 | 5.4 |
| 14.806 | 5.97820 | 19.6 |
| 15.48 | 5.71948 | 20.5 |
| 15.776 | 5.61288 | 18.7 |
| 16.059 | 5.51479 | 15.4 |
| 16.401 | 5.40024 | 50.1 |
| 16.623 | 5.32865 | 44.8 |
| 16.926 | 5.23406 | 43.6 |
| 17.572 | 5.04319 | 15.4 |
| 17.894 | 4.95294 | 15.4 |
| 18.338 | 4.83405 | 48.9 |
| 18.600 | 4.76648 | 50.4 |
| 18.961 | 4.67672 | 100 |
| 19.409 | 4.56959 | 58.2 |
| 20.462 | 4.33695 | 53.2 |
| 21.383 | 4.15201 | 12.6 |
| 21.846 | 4.06507 | 47.1 |
| 22.302 | 3.98297 | 58.1 |
| 22.779 | 3.90066 | 39.5 |
| 23.232 | 3.82568 | 35.6 |
| 24.055 | 3.69663 | 10.4 |
| 24.690 | 3.60288 | 17.4 |
| 25.388 | 3.50540 | 16.9 |
| 26.451 | 3.36697 | 33.9 |
| 27.178 | 3.27846 | 22.5 |
| 27.603 | 3.22900 | 20.6 |
| 28.472 | 3.13240 | 16.2 |
| 29.938 | 2.98221 | 14.8 |
| 30.180 | 2.95883 | 16.7 |
| 31.311 | 2.85449 | 21.8 |
| 31.861 | 2.80646 | 25.7 |
| 32.695 | 2.73674 | 14.6 |
| 33.177 | 2.69812 | 13.2 |
| 34.134 | 2.62459 | 8. |

22. A method for preparing crystalline Form V rosuvastatin zinc (2:1) salt according to claim 1, comprising providing a solution of rosuvastatin tert-butylamine salt in water or in a mixture of water and an alcohol comprising 1 to 6 carbon atoms, adding into said solution an aqueous solution of a zinc salt, at room temperature, and mixing and stirring said solution with 2 to 50-fold volume of water cooled to the temperature between −10 and 20° C., wherein amorphous rosuvastatin zinc (2:1) salt is formed, stirring the amorphous rosuvastatin zinc (2:1) salt at a temperature between −10 and 40° C. in 5 to 100-fold weight of water or in a mixture of water and an alcohol comprising 1 to 6 carbon atoms optionally containing 0.0001 to 0.01 molar equivalent amount of sodium hydroxide, calculated for the molar amount of rosuvastatin zinc salt of the Formula (I), for 1 to 48 hours, filtering the suspension, optionally repeating the stirring in 5 to 100-fold weight of water or in a mixture of water and an alcohol comprising 1 to 6 carbon atoms at a temperature between −10 and 40° C. for 1 to 48 hours, and optionally washing and drying the resultant product, which is crystalline Form III rosuvastatin zinc (2:1) salt, stirring the thus obtained product in 2 to 100-fold amount of water or in a mixture of water and an alcohol comprising 1 to 6 carbon atoms at a temperature between −10 and 40° C. for 1 to 168 hours, and isolating and optionally drying the product, which is crystalline Form V rosuvastatin zinc (2:1) salt.

23. A method according to claim 7, wherein the stirring, isolation and optional drying is carried out under an inert gas atmosphere, and the drying is carried out at a temperature between 0 and 30° C.

* * * * *